United States Patent [19]
Wu

[11] Patent Number: 5,083,414
[45] Date of Patent: Jan. 28, 1992

[54] METHOD FOR PACKAGING BIRTH CONTROL AND DISEASE PREVENTING DEVICE

[76] Inventor: Cheng M. Wu, 13726 Damian St., Cerritos, Calif. 90701

[21] Appl. No.: 657,160

[22] Filed: Feb. 15, 1991

[51] Int. Cl.⁵ .............................................. A61F 5/44
[52] U.S. Cl. ...................................... 53/429; 53/116; 128/844
[58] Field of Search ........................ 53/429, 116, 117; 128/844, 842; 604/352, 353, 349; 206/69

[56] References Cited

U.S. PATENT DOCUMENTS

| | | | |
|---|---|---|---|
| 3,290,855 | 12/1966 | Brinck et al. | 53/429 |
| 3,536,066 | 10/1970 | Ludwig | 128/132 |
| 4,597,494 | 7/1986 | Benoit | 53/429 X |
| 4,738,357 | 4/1988 | Martin et al. | 206/69 |
| 4,808,174 | 2/1989 | Sorkim | 128/644 |
| 4,827,693 | 5/1989 | Egea et al. | 53/429 X |
| 4,867,176 | 9/1989 | Lash | 128/830 |
| 4,875,491 | 10/1989 | Parrone | 128/844 |
| 4,888,007 | 12/1989 | Loeb et al. | 604/352 |
| 4,934,382 | 6/1990 | Barone, Jr. | 128/844 |
| 4,942,885 | 7/1990 | Davis et al. | 128/842 |
| 4,961,734 | 10/1990 | Kassman | 604/439 |
| 4,966,166 | 10/1990 | Leffler | 128/844 |

Primary Examiner—James F. Coan

[57] ABSTRACT

This invention relates to a method for packaging birth control and disease preventing device that has sheath and shield, and more particularly to a method having steps including: pleats the protecting shield toward tubular sheath forming a pleated star-like shape near the closed end of the sheath, bends the pleated star-like shape portion of the shield close to the tubular sheath forming a whirled-like cylindrical tubular, rolls the secure-and-rolled-up ring in the longitudinal direction toward the closed end of the sheath, and packs the rolled-up device into a water proof sealed container.

3 Claims, 7 Drawing Sheets

METHOD FOR PACKAGING BIRTH CONTROL AND DISEASE PREVENTING DEVICE

FIELD OF INVENTION

This invention relates to a method for packaging birth control and disease preventing device that has sheath and shield, and more particularly to a method having steps including: pleats the protecting shield toward tubular sheath forming a pleated star-like shape near the closed end of the sheath, bends the pleated star-like shape portion of the shield close to the tubular sheath forming a whirled-like cylindrical tubular, rolls the secure-and-rolled-up ring in the longitudinal direction toward the closed end of the sheath, and packs the rolled-up device into a water proof sealed container.

BACKGROUND OF THE INVENTION

As the population of the earth has increased tremendously each year, birth control is an important subject to pursuit. Another important problem facing the world today is the serious consequence of the transferable diseases obtained through sexual intercourse: from the annoying skin itch, to the awful venereal diseases, and sometimes to the deadly AIDS. It can be understood that effective method is still needed to provide more efficiency for avoiding the unwanted pregnancy; and more important, to reduce the possibility of obtaining the communicable sexual diseases when performing a sexual activity.

Various method has been developed for birth control, e.g. birth control pill and IUD, etc. However, using a condom for birth control is still a simple method for those people, who may have side effects when using other birth control methods or due to personal preference. While no contraceptive device provides 100% protection, condom when properly used can aid in the prevention of having pregnancy. For the purpose of preventing transmission of sexual diseases, condom is the simple and common useful device to achieve such goal. Conventional condom is easy to use, however, such condom can not protect the skin contact at the pubic area. Consequently, several condom with pubic shield have been invented. Some of those are: Puggard, Canadian Patent No. 1,158,507; Lee, U.S. Pat. No. 4,840,624; Sorkin, U.S. Pat. No. 4,808,174; Robichaud, U.S. Pat. No. 4,794,920; Grubman, U.S. Pat. No. 4,781,709, etc. Those device all have different shape and construction, but all have a pubic shield; and that pubic shield will increase the protecting for preventing disease transmission and reduce the chance of being pregnancy.

While the condom with pubic shield being invented, yet no one have taught how to pack those device in a easier and effective way. This invention is to show a method for packaging a condom with pubic shield; the method will allow such condom can be easier to pack, store, carry, and use.

Some of the prior art have shown different method for packaging a condom with protecting shield. Those prior art including: U.S. Pat. No. 4,966,166 to Leffler shows a condom packed in a pleated collapsed tube. U.S. Pat. No. 4,961,734 to Kassman discloses a condom packed in a collapsed condition with his condom applicator. U.S. Pat. No. 4,942,885 to Davis et al. discloses an article of clothing for use as a condom; that article allows the condom and the shield could be packed separately. U.S. Pat. No. 4,934,382 to Barone, Jr. discloses a condom packed in a rolled condition with manipulation tabs. U.S. Pat. No. 4,888,007 to Loeb et al. discloses a packaged public shield with a unitary condom showing in their FIG. 13. U.S. Pat. No. 4,875,491 to Parrone discloses a condom-holder device to be used with an accordion-like fold condom. U.S. Pat. No. 4,867,176 to Lash shows a female condom and an applicator received with a cup-like receptacle in his FIG. 16. U.S. Pat. No. 4,808,174 to Sorkin, he mentioned his plastic condom in a rolled condition as shown in his FIG.-3, however, his pubic shield still fully spread out as that shown in his FIG. 2. U.S. Pat. No. 4,738,357 to Martin et al discloses an element for receiving a condom. U.S. Pat. No. 3,536,066 to Ludwig discloses a condom of reversible proboscis shape that can be folded and unfolded as a bellows.

None of the above mentioned prior art has taught how to packaging a shield condom in a complete and easier process. The market is lacking of a method to show how to pack a condom with protecting shield in a simple and easier way to make it easier to store, carry, and use.

That special topic is what I present in my invention.

SUMMARY OF THE INVENTION

This invention is to show, step by step, a method of how to pack a condom with shield in a compact formation. Method is demonstrated by using three shield condom with different shape and size, and with different adhesive and fastening means. The showings are illustrated by using two circular and one square shape shield condoms. Other shield condom with different shape of shield, including but not limited to, such as elliptic, rectangle, triangle, trapezoid, pentagon, hexagon, octagon, other polygon, and irregular shape can be applied with the same technic.

DETAILED DESCRIPTION OF THE INVENTION

Details of invention, and the selected shield condoms for illustrating the packing technic, will be further understood upon reference to the drawings.

The method for packaging birth control and disease preventing device of this invention is shown in FIGS. 7 through 22. Before showing the packaging technic, three sampled condoms with shield are selected for illustrating the packaging technic. The selected sampled condoms are shown in FIGS. 1 through 6. These selected sampled condom are different between one and other in size and shape, but all having a pubic shield, adhesive or fastening means, and a secure-and-rolled-up ring.

Figure 1:
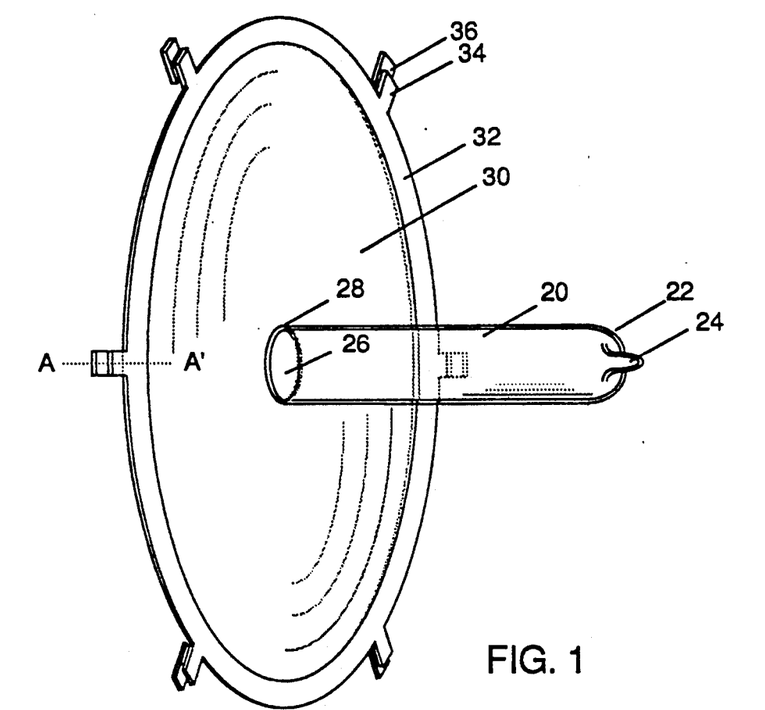
FIG. 1 is a perspective view of the first selected sampled shield condom to be used for illustrating the packaging technic. This condom has large protecting shield with adhesive tabs at the outer rim of the shield.
Figure 2:
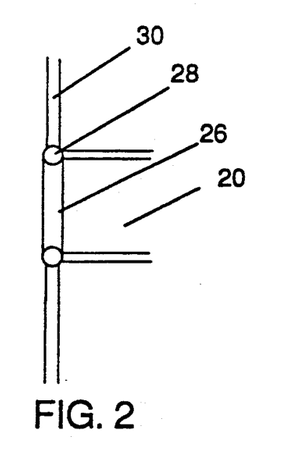
FIG. 2 is a cross-section view of the secure-and-rolled-up ring of FIG. 1 on a larger scale.
Figure 3:
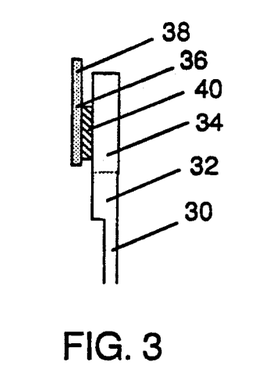
FIG. 3 is a cross-section view of one of the tabs of the first selected sample shield condom on the line A—A' in FIG. 1 on a larger scale.
Figure 4:
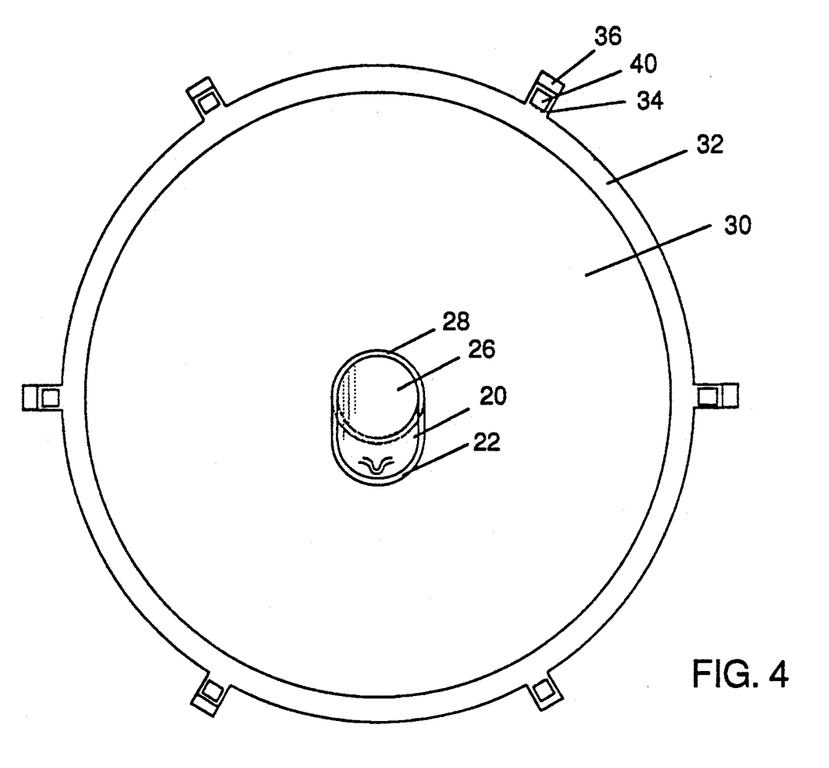
FIG. 4 is a front view of FIG. 1
Figure 5:
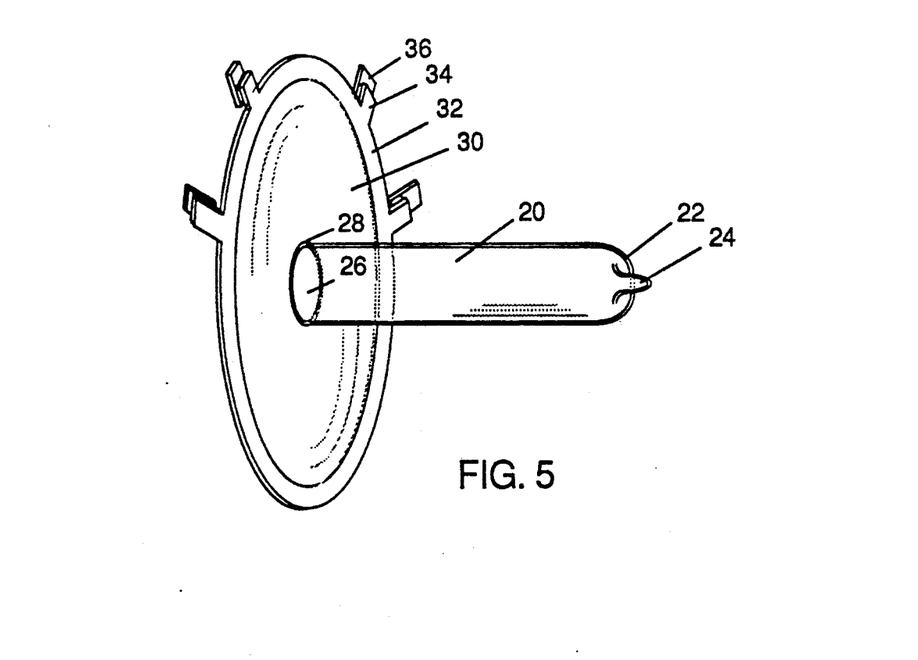
FIG. 5 is a perspective view of the second selected sampled condom to be used for illustrating the packaging technic. This condom has a smaller protecting shield than that showing in FIG. 1.
Figure 6:
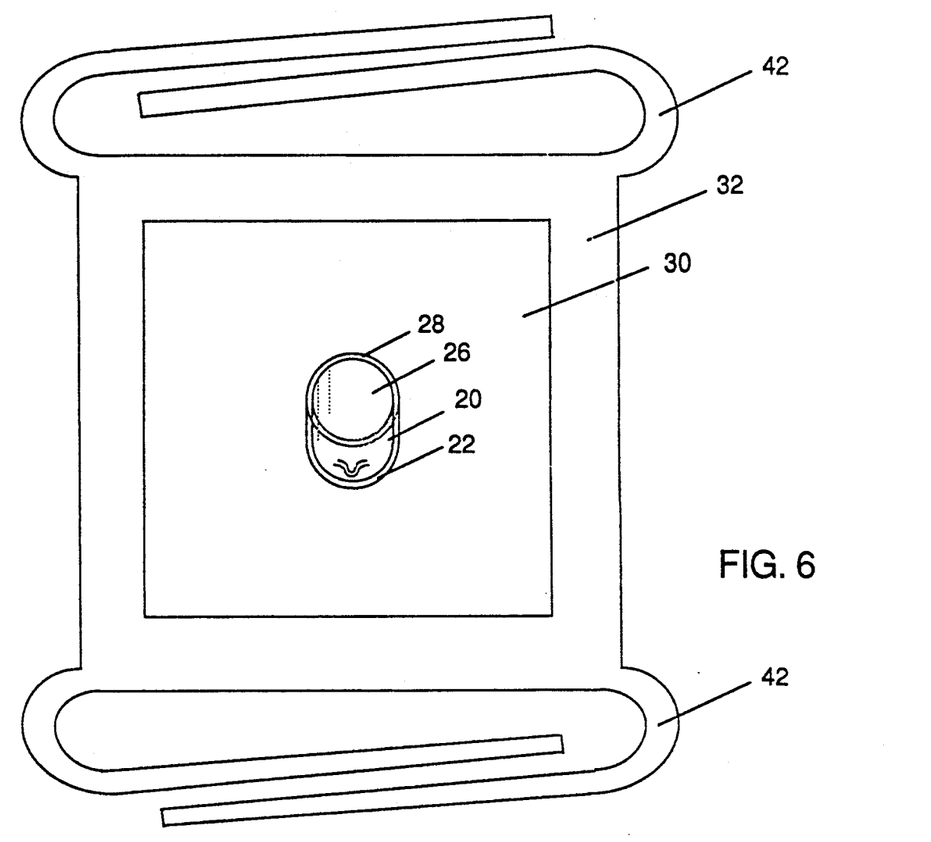
FIG. 6 is a perspective view of the third selected sampled condom to be used for illustrating the packaging technic. This condom has a square protecting shield and has long strands or tapes.
Figure 7:
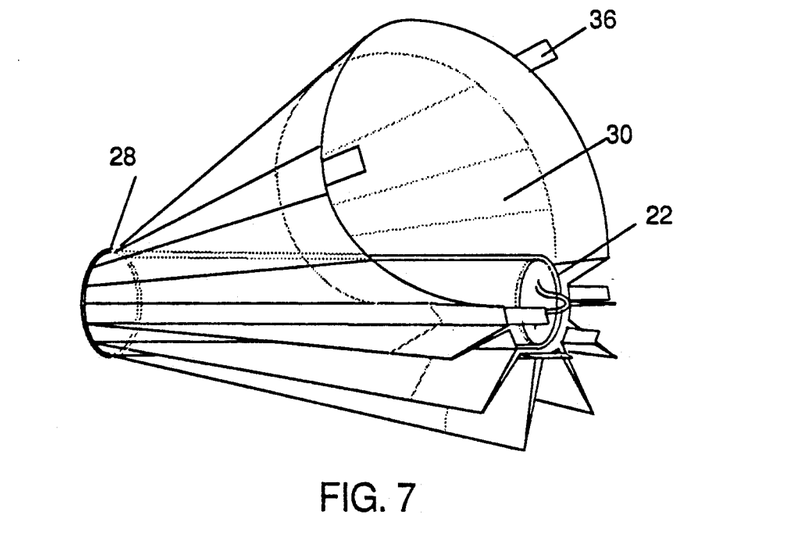
FIG. 7 is a perspective view of the first selected sampled condom being packed in step one.
Figure 8:
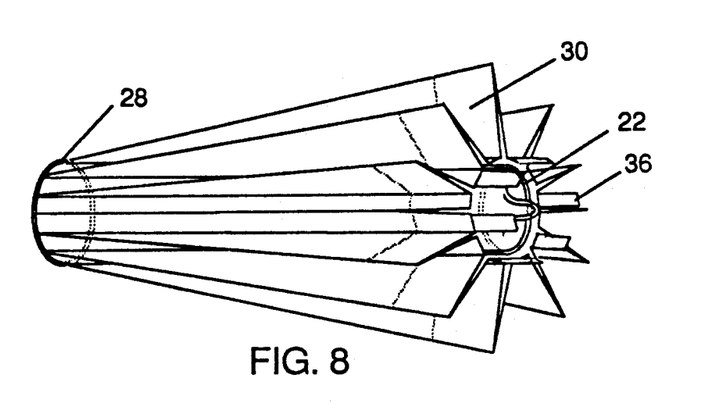
FIG. 8 is a perspective view of the first selected sampled condom being packed in the completion of step one.
Figure 9:
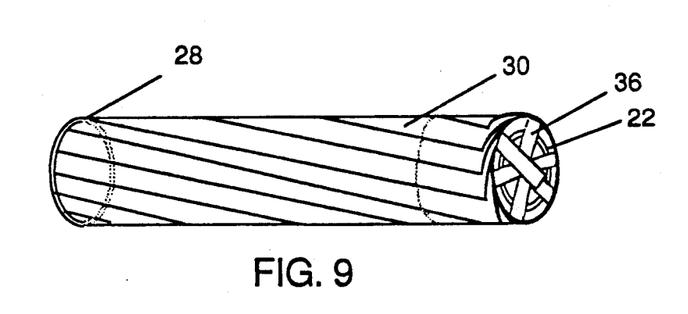
FIG. 9 is a perspective view of the first selected sampled condom being packed in step two.
Figure 10:
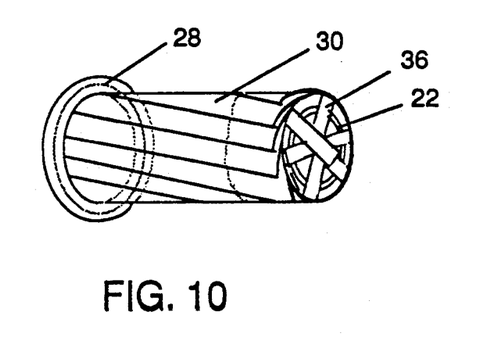
FIG. 10 is a perspective view of the first selected sampled being packed in step three.
Figure 11:
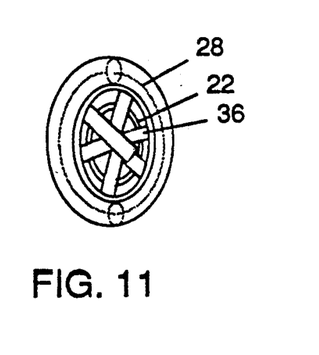
FIG. 11 is a perspective view of the first selected sampled condom being packed in the completion of step three.
Figure 12:
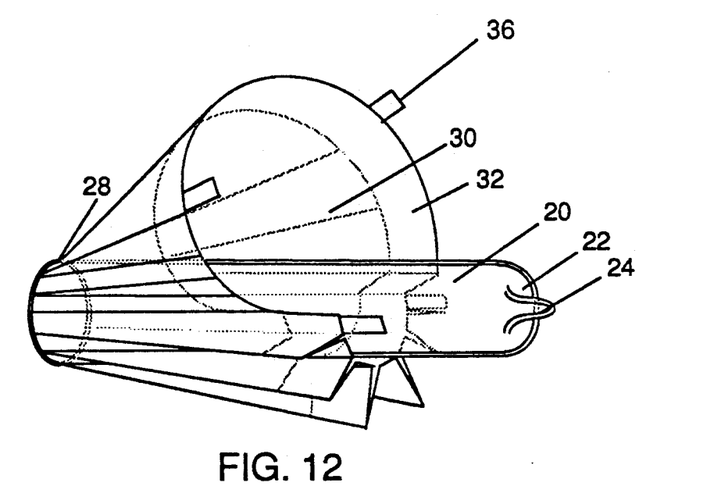
FIG. 12 is a perspective view of the second selected sampled condom being packed in step one.
Figure 13:
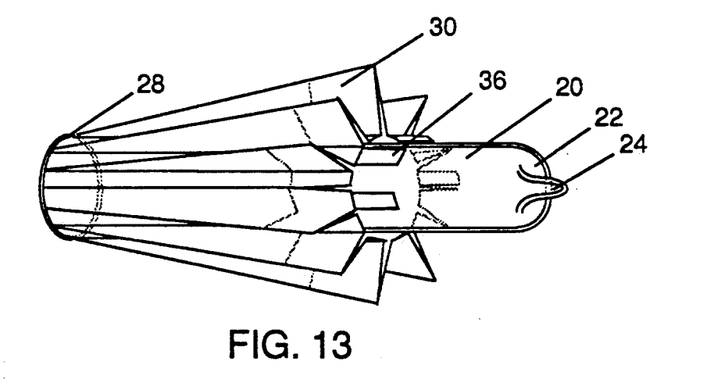
FIG. 13 is a perspective view of the second selected sampled condom being packed in the completion of step one.
Figure 14:
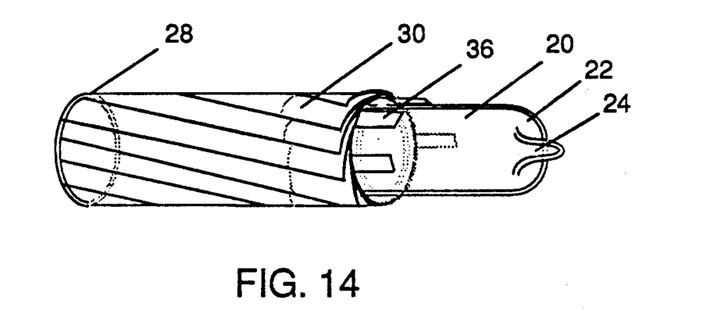
FIG. 14 is a perspective view of the second selected sampled being packed in step two.
Figure 15:
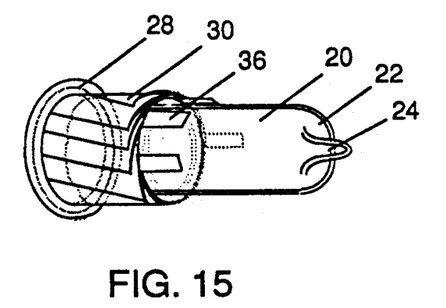
FIG. 15 is a perspective view of the second selected sampled being packed in step three.
Figure 16:
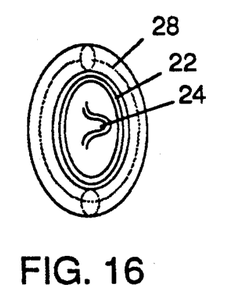
FIG. 16 is a perspective view of the second selected sampled condom being packed in the completion of step three.
Figure 17:
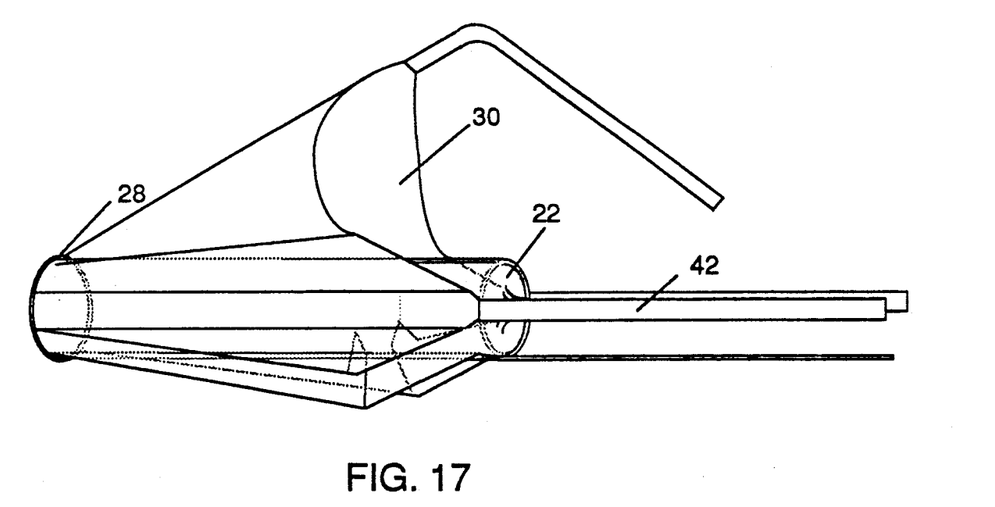
FIG. 17 is a perspective view of the third selected sampled condom being packed in step one.
Figure 18:
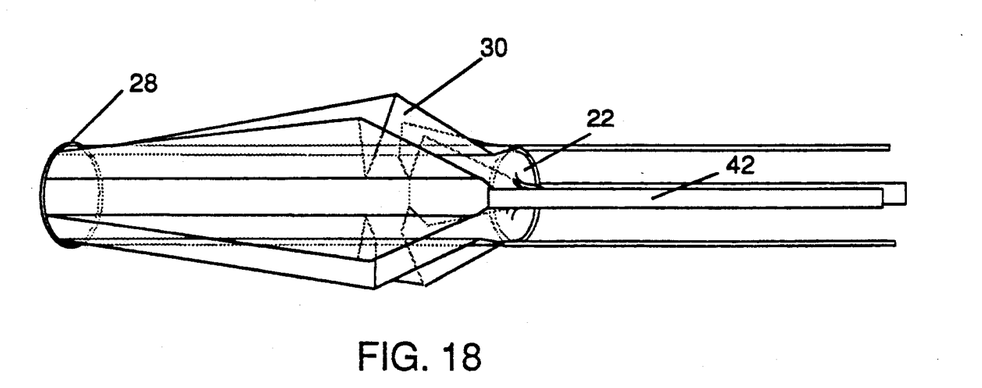
FIG. 18 is a perspective view of the third selected sampled condom being packed in the completion of step one.
Figure 19:
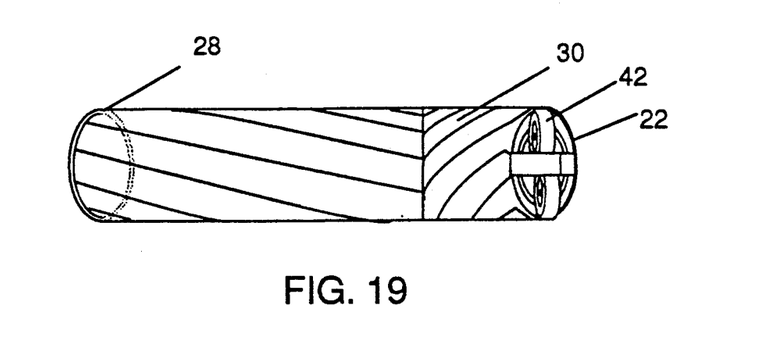
FIG. 19 is a perspective view of the third selected sampled condom being packed in step two.
Figure 20:
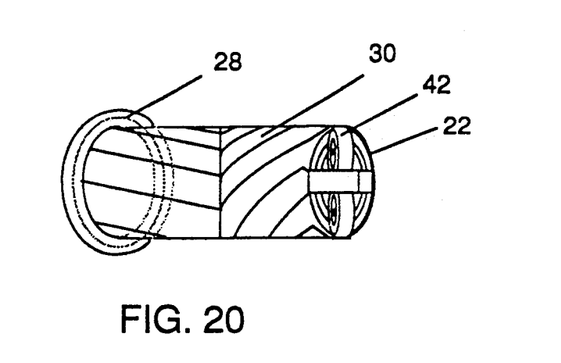
FIG. 20 is a perspective view of the third selected sampled condom being packed in step three.
Figure 21:
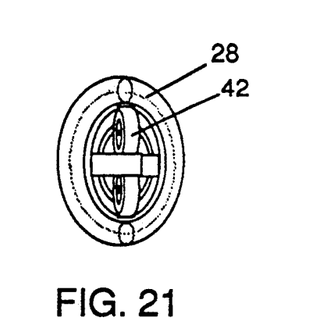
FIG. 21 is a perspective view of the third selected sampled condom being packed in the completion of step three.
Figure 22:
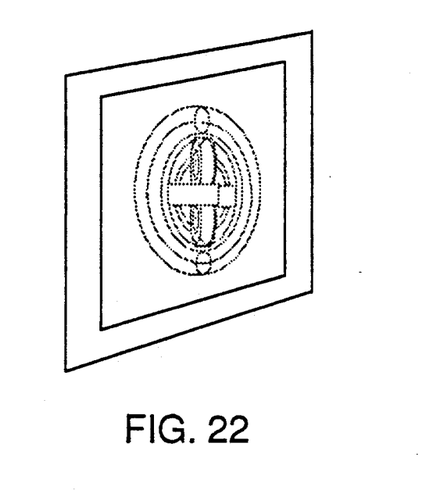
FIG. 22 is a perspective view of the rolled-up shield condom being packed in a sealed container.

FIG. 1 shows the general feature of the first selected sampled shield condom. There shown a condom has a resilient and flexible body construction with an elongated thin-walled tubular portion 20. The tubular portion 20 has a closed end 22, which may or may not have a special receptacle end 24. The tubular condom also have an open end 26 for entering the male penis. The open end 26 is surrounding by an elastics secure-and-rolled-up ring 28 for tightening the penis and for rolling up the device when in packaging before the use. An large elastic circular flat shield 30, is integrated from the secure-and-rolled-up ring 28. The outer edge of the flat shield 30 may have a thicker rim 32 for strengthen the flat shield when it is spread out in used. The condom has tabs for adhesive to the human body. Six tabs 34, may have more or less, are shown in the FIGS. 1 and 4. FIG. 2 is a cross-section of the secure-and-rolled-up ring of FIG. 1 on a larger scale; the secure-and-rolled-up ring will be used for rolling the tubular sheath during packaging process. FIG. 3 shows a cross-section view of one of the tabs of the first selected sampled shield condom on the line A—A' in FIG. 1 on a larger scale; the tabs is used for adhesive the device to the human body. These tabs are integrated from the outer edge of the flat shield 30. These tabs has an area of about 2 square centimeters, more or less, with about 1 square centimeter adhesive 40 coated on it. A removable paper, or plastic peeling sheet, 36 designed to cover the adhesive when the condom is not in used. The cover paper, or plastic peeling sheet, has an leading portion 38 for easily peeling away from the adhesive when in used. The tabs 34 are designed located in equally spacing at the outer edge of the circular flat shield 30 as shown in FIG. 4. FIG. 4 is a front view of FIG. 1. A second selected sampled shield condom with different size of the protecting shield and different design of the tab locations is illustrated in FIG. 5. FIG. 6 shows a third selected sampled shield condom to be used for illustrating the packaging technic. This sampled condom has a square pubic protecting shield 30 with long strands or tapes 42 for using as fastening means. FIG. 7 shows the first step of packaging: the circular flat shield 30 is being first pleated toward the tubular portion 20. FIG. 8 shows the continuation of the first step of packaging: the whole circular flat shield 30 being bent and pleated toward the tubular portion and form a general star-like shape when look from the closed end, the tabs are lain down and extended around the closed end 22. FIG. 9 shows the second step of packaging: the pleated star-like shape portion, the shield, is bent and rolled into a whirled-like cylindrical shape with all the flat shield 30 now being pleated and bent closed to the tubular; and all the tabs together with the covering papers 36 are folded over the closed end 22. FIG. 10 shows the third step of the packaging: it starts from the open end and using the secure-and-rolled-up ring 28 to rolling up the tubular toward the closed end 22, the figure shows the rolling up to the half way of the tubular. FIG. 11 shows the continuation of rolling up the device until the secure-and-rolled-up ring 28 reached the closed end 22. FIG. 11 is a completion of the rolled up process and that rolled up condom is ready to be packed into a conventional water proof protective sealed container. FIGS. 12 through 16 show the steps of packing the second selected sampled condom. The sampled condom features a smaller circular flat shield which having a measurement from the rolled up ring 28 to the outer edge of the thicker rim 32 is about two third of the tubular length from the open end 26 to the closed end 22. FIG. 12 shows the first step of packaging: the circular flat shield 30 is being first pleated toward the tubular portion 20; FIG. 13 shows the continuation of the first step of packaging: the whole circular flat shield 30 being folded and pleated toward the tubular portion and form a general star-like shape when look from the closed end, and all the tabs and covering papers 36 are placed longitudinally over the tubular 20. FIG. 14 shows the second step of packaging: the pleated star-like shape portion 30, the shield, is then bent and rolled into a whirled-like cylindrical shape with all the flat shield 30 now being pleated and bent closed to the tubular tube 20. FIG. 15 shows the third step of rolling up the tubular; starting from the open end 26 and using the secure-and-rolled-up ring 28 to roll the whirled-like tubular tube toward the closed end 22. FIG. 15 shows the half way of the rolling. FIG. 16 shows the continuation of the rolling up until the secure-and-rolled-up ring 28 reached the closed end 22. FIG. 16 is a completion of the rolled up process and that rolled up condom is ready to be packed into a conventional water proof protective sealed container. FIGS. 17 through 21 show the steps of packing the third selected sampled condom. The sampled condom features a square flat shield having long strands or tapes 42 using for fastening to the human body when in use. FIG. 17 shows the first step of packaging: the square flat shield 30 is being first pleated toward the tubular portion 20; FIG. 18 shows the continuation of the first step of packaging: the whole square flat shield 30 being folded and pleated toward the tubular portion and form a general star-like shape when look from the closed end, and all the strands or tape 42 are extended parallelly in the longitudinal direction beyond the closed end of the tubular 20. FIG. 19 shows the second step of packaging: the pleated star-shape portion 30, the shield, is then bent and rolled into a whirled-like cylindrical shape with all the flat shield 30 now being pleated and bent closed to the tubular tube 20, and all the strands or tape 42 are rolled or folded closing to the closed end of the tubular 20. FIG. 20 shows the step of rolling up the tubular; starting from the open end 26 and using the secure-and-rolled-up ring 28 to roll the whirled-like tubular tube toward the closed end 22. FIG. 20 shows the half way of the rolling. FIG. 21 shows the continuation of the rolling up until the secure-and-rolled-up ring 28 reached the closed end 22. FIG. 21 is a completion of the rolled up process and that rolled up condom is ready to be packed into a conventional water proof protective sealed container. FIG. 22 shows the last step for packaging; the rolled-up shield condom, shown here using the result of FIG. 21 but also good for the results of FIGS. 11 and 16, being packed into a conventional water proof protective sealed container using the well-known condom packaging technic.

From the foregoing mentioned figures, although a limited number of illustration of the invention have been described in details, it should be realized that modifications and other similar steps of the invention features may be constructed. It should be realized that form a star-like shape in the first step is not limited to form a star-like shape with a fixed number of spines or points. Although showing in the FIG. 8 and FIG. 18 are results having a star-like formation of 12 and 8 spines or points when look from the condom closed end; it is possible to bend and pleat the pubic shield and forming the star-like formation with different number of spines or points. For example, with only 6, 5 or 4 spines or points. In the lower limits, forming a star-like formation with 3 spines or points is possible. Even in the lowest limit, forming a star-like formation with only 2 spines or points is still possible which is a result of the pubic protecting shield with a single fold toward circular tubular tube. It should be pointed-out that the lower the star-like spine number, the more deviation shape from a circular ring after the whole shield condom has been rolled-up. After forming the star-like shape, it should be realized that the bend and roll of the pleated star-like shape into a whirled-like cylindrical formation closing to the tubular tube is not limited to one direction. It is possible to roll the star-like spine in either clock-wise or counter-clock-wise when look from the closed end of the tubular. The rolling is not limited to all spines having the same direction. Some of those may be rolled in one direction, and the rest in other direction. A combination of any of these features can easily be created another packaging process within the scope of the invention. It is intended that the foregoing disclosures and drawings shall be considered only as illustrations of the principles of the invention.

For my invention, the size and shape of the protecting shield herein specified are not critical, and any condom with a pubic shield having similar structure, that is having a pubic shield and a secure-and-roll-up ring would be suitable for packaging by using the invention method.

From the foregoing, it should be evident that the invention provides a new method for packaging a birth control and disease preventing device. The method will provide more compact result to package the device and therefore provide effective results to store, carry and use a shield condom, which could be more useful for the birth control and having more protection against the transmission of venereal diseases during copulation when compared with the conventional condom.

I claim:

1. A method for packaging birth control and disease preventing device which having a tubular sheath and a protecting shield and a secure-and-roll-up ring and adhesive tabs, and said tubular sheath having a closed end and an open end, and said secure-and-roll-up ring is integrated with said protecting shield at about the center of said shield and integrated with said tubular sheath at said open end of said sheath, and said device is made of thin flexible and resilient materials used in presently available condoms, comprising the steps of:

(a) pleating said protecting shield toward said tubular sheath forming a pleated star-shape with a plurality of points, or spines, near the closed end of said sheath, placing said adhesive tabs in the longitudinal direction along said sheath;

(b) bending said pleated star-shape portion of said shield close to said tubular sheath forming a whirled-like cylindrical tubular, and bending said adhesive tabs inwardly to said closed end of said sheath if said tabs extended beyond said closed end of said tubular sheath;

(c) starting from said open end of said tubular sheath and using said secure-and-rolled-up ring rolling said whirled-like cylindrical tubular in the longitudinal direction toward said closed end of said tubular sheath forming a general doughnut-like rolled-up formation near said closed end with said closed end at the center; and (d) placing said rolled-up formation into a container and sealing said container.

2. A method for packaging birth control and disease preventing device which having a tubular sheath and a protecting shield and a secure-and-roll-up ring and fastening strands or tapes, and said tubular sheath having a closed end and an open end, and said secure-and-roll-up ring is integrated with said protecting shield at about the center of said shield and integrated with said tubular sheath at said open end of said sheath, and said device is made of thin flexible and resilient materials used in presently available condoms, comprising the steps of:

(e) pleating said protecting shield toward said tubular sheath forming a pleated star-shape with a plurality of points, or spines, near the closed end of said sheath, placing said strands or tapes in the parallel formation and in the longitudinal direction extended beyond said closed end of said sheath;

(f) bending said pleated star-shape portion of said shield close to said tubular sheath forming a whirled-like cylindrical tubular, and rolling and folding the portion of said fastening strands or tapes, that extended beyond said close end of said sheath, inwardly and placing the rolled and folded strands or tapes close to said closed end of said sheath;

(g) starting from said open end of said tubular sheath and using said secure-and-rolled-up ring rolling said whirled-like cylindrical tubular in the longitudinal direction toward said closed end of said tubular sheath forming a general doughnut shape rolled-up formation near said closed end with said closed end at the center; and (h) placing said rolled-up formation into a container and sealing said container.

3. A method for packaging birth control and disease preventing device which having a tubular sheath and a protecting shield and a secure-and-roll-up ring and adhesive means and linen, and said adhesive means and linen are located within the outer rim of said shield, and said tubular sheath has a closed end and an open end, and said secure-and-roll-up ring is integrated with said protecting shield at about the center of said shield and integrated with said tubular sheath at said open end of said sheath, and said device is made of thin flexible and resilient materials used in presently available condoms, comprising the steps of:

(i) pleating said protecting shield, together with said adhesive means and linen, toward said tubular sheath forming a pleated star-shape with a plurality of points, or spines, near the closed end of said sheath;

(j) bending said pleated star-shape portion of said shield and the portion of adhesive means and linen close to said tubular sheath forming a whirled-like cylindrical tubular;

(k) starting from said open end of said tubular sheath and using said secure-and-rolled-up ring rolling said whirled-like cylindrical tubular in the longitudinal direction toward said closed end of said tubular sheath forming a general doughnut-like rolled-up formation near said closed end with said closed end at the center; and (l) placing said rolled-up formation into a container and sealing said container.

* * * * *